United States Patent [19]

Fernwood et al.

[11] Patent Number: 4,994,166
[45] Date of Patent: Feb. 19, 1991

[54] SINGLE APPARATUS FOR SLAB GEL ELECTROPHORESIS AND BLOTTING

[75] Inventors: George G. Fernwood, Larkspur; Efrem G. Hernandez, San Rafael; Frank R. Witney, Novato, all of Calif.

[73] Assignee: Bio-Rad Laboratories, Inc., Hercules, Calif.

[21] Appl. No.: 397,065

[22] Filed: Aug. 22, 1989

[51] Int. Cl.[5] .................. G01N 27/26; B01D 57/02
[52] U.S. Cl. .......................... 204/299 R; 204/182.1; 204/182.8; 204/301
[58] Field of Search ............... 204/299 R, 301, 182.1, 204/182.8, 180.1, 182.3

[56] References Cited

U.S. PATENT DOCUMENTS 4,622,124 11/1986 Kreisher et al. ............ 204/299 R X

FOREIGN PATENT DOCUMENTS 313293 4/1989 European Pat. Off. ........ 204/299 R

OTHER PUBLICATIONS

Reijenga, J. C.; Verheggen, Th. P .E. M.; Everaerts, F. M. "Fluorescence Emission and Fluorescence Quenching as Detection Methods in Isotachophoresis" Journal of Chromatography, 283 (1984), 99–111.

*Primary Examiner*—John F. Niebling
*Assistant Examiner*—John S. Starsiak, Jr.
*Attorney, Agent, or Firm*—Townsend and Townsend

[57] ABSTRACT

Electrophoretic separation in a slab gel and blotting of the resulting zone pattern onto a membrane are both performed in a single tank cell which contains separation electrodes along opposing vertical walls and blotting electrodes horizontally arranged above and below the level designated for the gel placement. The blotting electrode situated below the gel is an array of parallel wires arranged to simulate a plate electrode. The cell is operated in separatory and blotting modes, in which the separation and blotting electrodes, respectively, are separately energized. During the separatory mode, the wires in the array forming the lower blotting electrode are electrically isolated from each other to permit each to adjust to the voltage of the buffer immediately surrounding it.

19 Claims, 3 Drawing Sheets

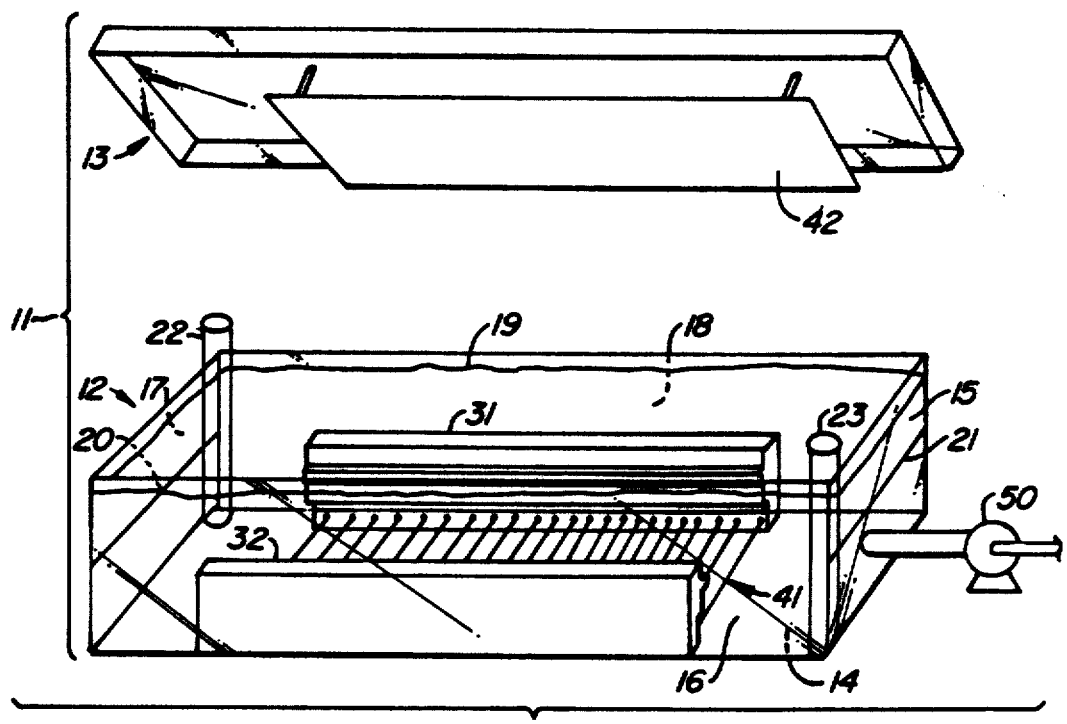
FIG._1.
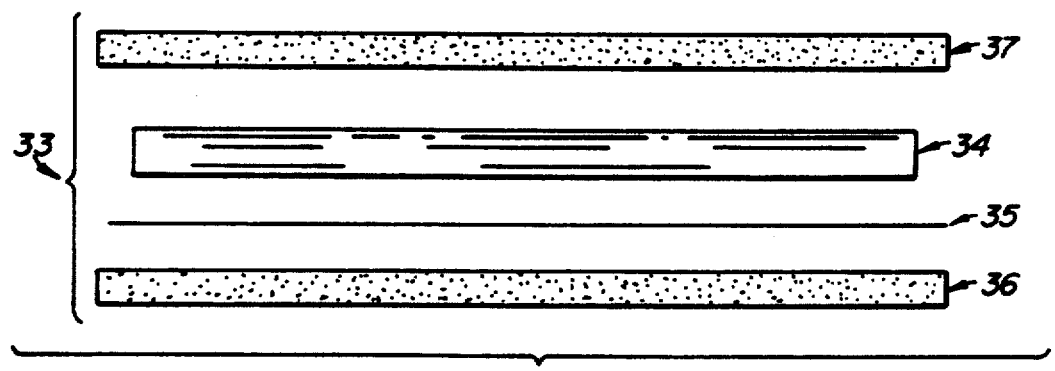
FIG._2.

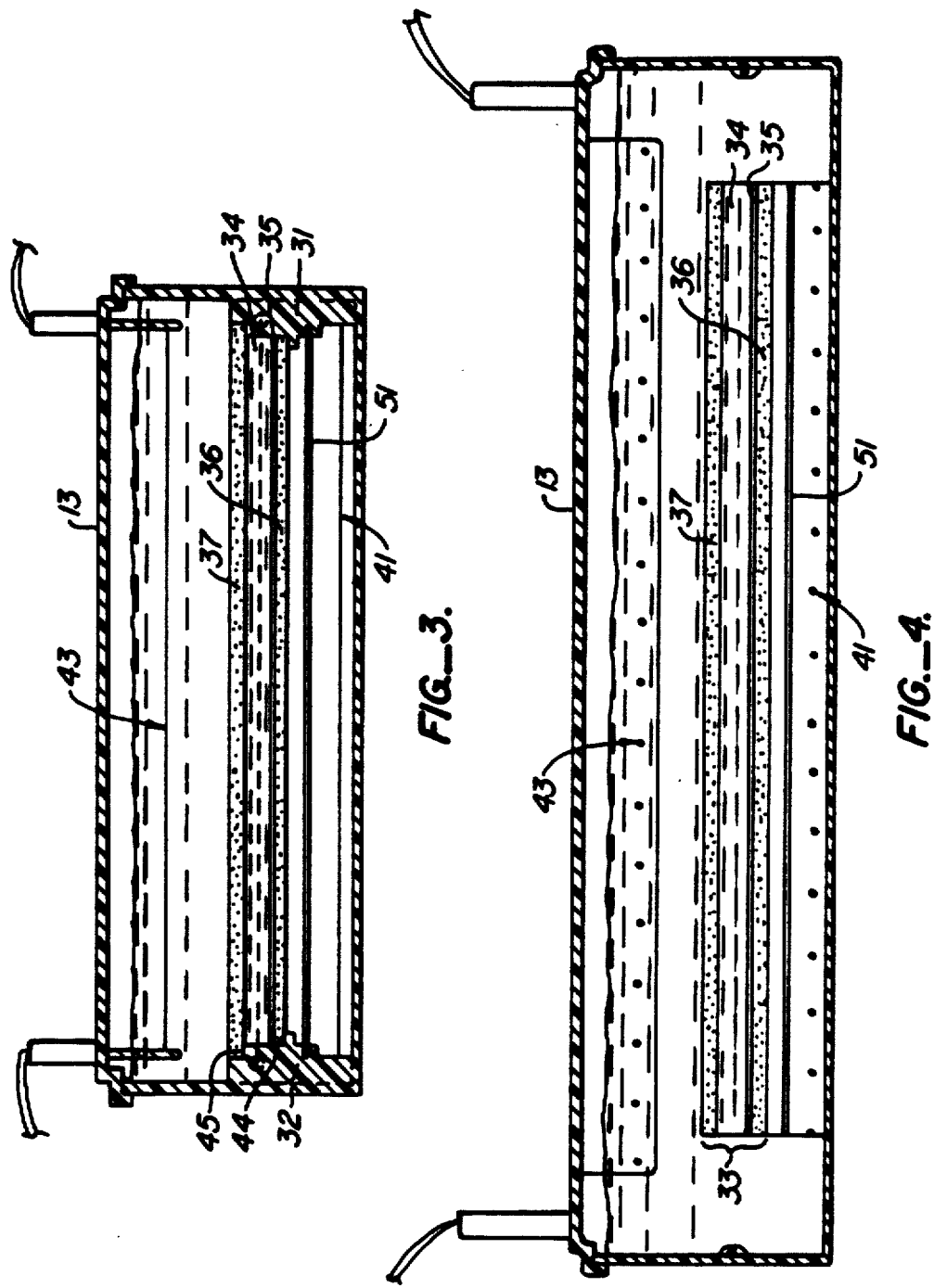

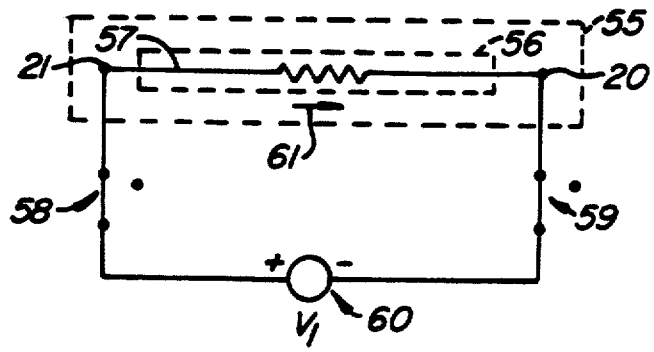
FIG._5a.
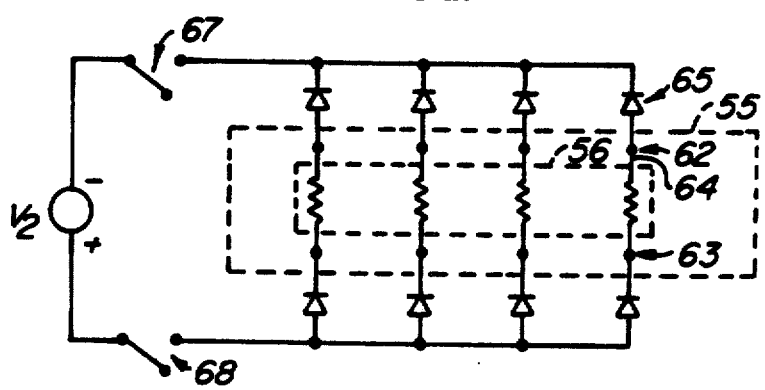
FIG._5b.
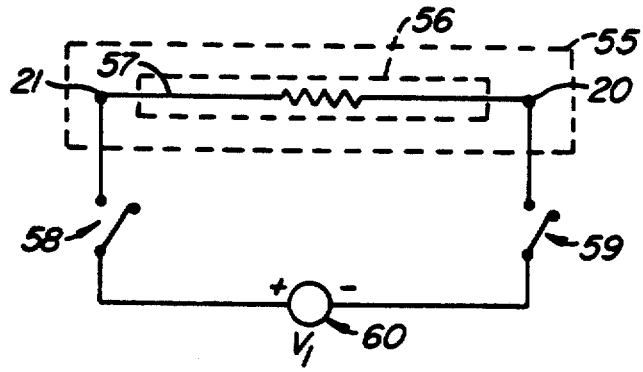
FIG._6a.
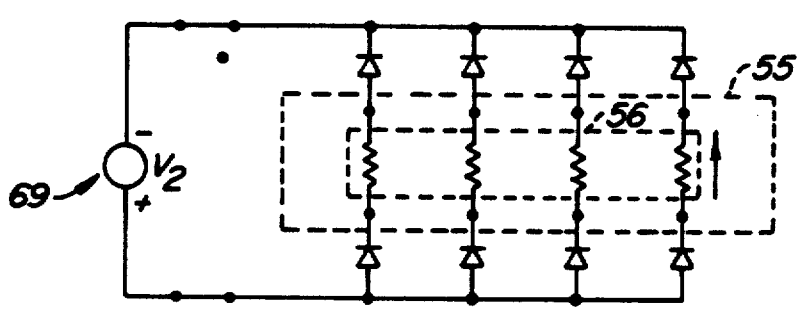
FIG._6b.

SINGLE APPARATUS FOR SLAB GEL ELECTROPHORESIS AND BLOTTING

This invention is in the field of methods and apparatus for electrophoresis The particular field to which this invention applies is slab gel electrophoresis and the transfer of electropherograms onto the surface of a treated paper or membrane for analytical or preparative purposes

BACKGROUND AND SUMMARY OF THE INVENTION

Electrophoretic separations of such species as DNA, RNA or proteins in slab gels are generally followed by the blotting or immobilization of the separated species onto the surface of a treated paper or membrane The zone pattern of the separated species is maintained during the blotting procedure, and the blotting permits one to preserve the zone pattern or to separate and isolate the individual zones, thus serving an important function for both analytical and preparative purposes Separation and blotting are commonly performed in two separate pieces of apparatus, requiring a certain amount of manual manipulation by the user. Capillary blotting, based on the studies reported by Southern, E.M., *J. Mol. Biol.*, 98. 503 (1975), relies on the liquid absorbent character of filter papers and similar materials to draw buffer solution from one side of the gel to the other, the buffer solution drawing the solute zones along with it. The solute zones are immobilized by the treated paper or membrane upon contact, resisting further movement Vacuum transfer is an alternative to capillary blotting, and uses a pressure differential to cause the bulk migration of buffer solution across the gel. The mechanism by which the solute zones are extracted from the gel and immobilized on the paper or membrane is the same as in capillary blotting. The third known alternative is electrophoretic blotting, where the transfer is performed electrophoretically by imposing an electric potential in the direction perpendicular to the plane of the gel.

Each of these techniques has inherent advantages. In capillary blotting, the speed and quality of the transfer depend upon the user's ability to avoid air bubbles in the liquid migration path. In addition, capillary blotting is a slow procedure, generally requiring 8-24 hours unless the absorbing sheets at the downstream side of the flow direction are periodically replaced. Even then, capillary transfers generally require a minimum of about 4 hours. A vacuum transfer generally requires 2-4 hours, plus an additional hour to perform a series of gel soaks for various purposes prior to the application of the vacuum. Electrophoretic transfer is the fastest of the three, permitting transfers in as little as ten minutes. Each of these procedures, however, involves removing the gel from the separation cell and physically placing it in the blotting apparatus, which steps are performed manually by the user. Gels are very delicate, and handling invariably raises a risk of damage to the gel. In addition, the physical transfer of the gel between the two pieces of apparatus is time consuming.

An apparatus has now been developed which permits electrophoretic separation in a slab gel followed by transfer of the separated zone pattern to an immobilizing sheet or membrane with no intervening movement of the slab gel required. The electrophoretic separation is performed in a submarine-type cell, equipped with additional electrodes appropriately placed for electrophoretic transfer of the separated zones in the direction normal to the gel once the separation is complete. The gel is arranged horizontally in the cell where it is submerged in buffer solution between a pair of elongate separation electrodes arranged to cause sample migration along the plane of the gel. Blotting electrodes above and below the gel are then energized to impress a potential normal to the gel which causes the separated species to migrate out of the gel onto an adjacent membrane. A plate electrode underneath the gel is simulated by an array of exposed wires, parallel to each other as well as to the separation electrodes.

The cell operates in a separatory mode and a blotting mode, the passage from one to the next being governed by an electric switch arranged such that the field established by the separation electrodes during the separatory mode experiences no interference from the blotting electrodes. When the cell is in the separatory mode, the wires in the array are electrically isolated from each other to permit each to adjust to the voltage of the buffer immediately surrounding it, according to the distance of each wire from the separation electrodes. In the blotting mode, the wires in the array are electrically connected, and their spacing is close enough to simulate, in the region of the gel, an electrical field created by a continuous plate electrode.

Since the upper blotting electrode can be handled without disturbing the gel, it may assume any of a variety of forms. One such form is an array of electrode wires similar to the array beneath the gel. Other possibilities are disclosed below.

A uniform transfer of separated solutes during the blotting phase of the operation is achieved by preventing bubbles generated during blotting from coming to rest against the membrane. Various embodiments of the invention are described for preventing bubbles generated at the lower blotting electrodes from reaching the membrane or from stagnating and accumulating beneath the membrane. A porous plate serves as a support for both the membrane and the gel while permitting full fluid and electrical contact of the membrane and gel with the buffer solution underlying both.

Further features, embodiments and advantages of the invention are described below.

BRIEF DESCRIPTION OF THE DRAWINGS

FIG. 1 is a perspective view of an electrophoresis cell illustrating one embodiment of the present invention, in a form of a submarine cell with lid raised, lacking the gel stack components;

FIG. 2 is an exploded side elevation view of a gel stack for possible use with the cell shown in FIG. 1:

FIG. 3 is a transverse cross-sectional view of an elongate submarine cell, similar to that shown in FIG. 1 except for substitution of a wire array for the upper electrode plate of FIG. 1:

FIG. 4 is a longitudinal cross-sectional view of the cell shown in FIG. 3:

FIG. 5 is an electrical diagram of a switching circuit suitable for an electrode arrangement such as that shown in FIGS. 3 and 4, shown in the separation mode;

FIG. 6 is an electrical diagram of the switching circuit of FIG. 5, shown in the blotting mode.

DETAILED DESCRIPTION OF THE INVENTION AND PREFERRED EMBODIMENTS

The principles of the present invention are most conveniently embodied in an electrophoresis cell designed for electrophoresis slab gels arranged horizontally, and particularly slab gels which are submerged in buffer during the run. Commonly termed submarine cells, these cells contain exposed cathode and anode wires also submerged in the buffer, laterally spaced from the gel along the direction of sample migration. A gel and buffer solution of the same resistivity are used, giving rise to an equal flow of current through both.

A form of submarine cell embodying the principles of the present invention is illustrated in FIG. 1. The submarine cell 11 consists of a liquid receptacle or tank 12 and a lid 13 to fit over the tank 12 and enclose its open top. The tank has a floor 14 and four raised sides 15, 16, 17, 18, and is shown filled with buffer solution up to a liquid level 19. The tank in this embodiment is in the shape of an elongated rectangle, two of the opposing sides 16, 18 of which are longer than the other two 15, 17. For convenience, the longer raised sides 16. 18 will be referred to herein as side walls, and the shorter 15, 17 as end walls. A cathode 20 and anode 21 are secured to the two end walls 17, 15, respectively, with appropriate electrical connections 22. 23 to supply electric power to each.

Support brackets 31, 32 are placed in the tank interior along side walls 18 and 16, respectively. These support brackets are designed to hold a gel stack 33 which includes the slab gel, immobilization membrane, and liquid-penetrable supporting plate, above the tank floor 14. An exploded view of one example of a gel stack which may be used in accordance with the present invention is shown in a side view in FIG. 2. The gel 34 is a typical slab gel, rectangular in shape. A typical gel material such as agarose or polyacrylamide may be used and the dimensions of the gel may vary widely, depending on the number of samples to be run simultaneously, the type of sample, and the sample volume, provided of course that the length and width of the gel will fall completely within the spacing between the two support brackets 31, 32. Underneath the gel is an immobilization membrane 35, which may be of any of a wide range of blotting materials, such as paper, nitrocellulose, nylon, and other materials, as well as such materials in treated or derivatized form, as well known among those skilled in the art. The use of the membrane 35 and the method by which the sample solute pattern in the gel 34 is transferred to the membrane is discussed in detail below.

Further components of the gel stack 33 are a lower support plate 36, which is sufficiently porous to provide ample contact of the buffer solution beneath the stack with the gel 34 and membrane 35 in the stack. The pores are sufficiently small, however, to hold the gel and membrane flat above it. The support plate 36 is made of a hydrophilic material to encourage full wetting by the buffer solution and facilitate the escape of any bubbles which might appear inside the pore network.

The final component of the gel stack is an upper plate 37, which functions primarily during the blotting phase, i.e., the transfer of the separated solutes from the gel 34 to the blotting membrane 35. This as well will be discussed in further detail below.

The gel stack 33 is generally rectangular in shape, conforming to the length of the support brackets 31, 32 (FIG. 1) and the spacing between them. The lower plate 36 of the stack rests on ledges appropriately positioned along the support brackets, and shown and described in more detail below in connection with FIGS. 3 and 4. The tank 12 provides for clearance at the two end walls 15. 17 between the electrodes 20. 21 and the end edges of the gel stack, to allow a uniform and stable electric field in the region of the gel stack.

The separation electrodes 20, 21, which are shown as wire electrodes in the drawings, may be of any configuration which will provide a uniform electric field through the horizontal center plane which is at the mid-thickness of the gel, i.e., unidirectional throughout the center plane in the desired direction of migration of the sample components during the separation mode, and of uniform field intensity throughout the center plane as well. Wire electrodes which are fixed at a height coplanar with the center plane as shown in the drawings are thus one example. Plate electrodes along the walls extending the entire length of the walls are another example. It will be noted that plate electrodes create a uniform electric field at any height between the plates. Plate electrodes must be constructed such that they do not interfere with the current flow in the region of the gel during the blotting mode. They must therefore be sufficiently narrow in the vertical direction or laterally spaced from the gel that they neither create a current path around the gel rather than through it, nor interfere with the potential gradient through the gel. Alternatively, they may be arranged in the apparatus in such a manner that they can be removed or isolated from the system during the blotting mode.

When wire electrodes are used as the separation electrodes, the dimensions of the components of the gel stack 33, the structure of the support brackets 31, 32, and the height of the separation electrodes above the tank floor 14 are selected such that the separation electrodes define a plane located parallel to and midway between the lower and upper plates 36. 37 of the gel stack, level with the midpoint of the gel thickness.

Turning now to the blotting mode of the apparatus, attention is once more directed to FIG. 1. Blotting is achieved by electrophoretic transfer using blotting electrodes positioned above and below the gel. The blotting electrodes are energized with current after sufficient solute separation in the horizontal direction has occurred, and the power to the separation electrodes 20. 21 has been turned off. The blotting electrodes are arranged and electrically connected in such a way that, when not in use, they do not interfere with the electric field created by the separation electrodes 20, 21.

The lower blotting electrode as shown in FIG. 1 is an array of parallel exposed wires 41, each also running parallel to the separation electrodes 20, 21. These wires 41 are set in a horizontal plane on or in close proximity to the floor 14 of the tank. The wires are closely enough spaced to simulate a plate electrode in terms of the electric field which they create in the region of the gel stack when the latter is resting on the support brackets 31. 32. These wires are connected in such a manner that they can be electrically isolated from each other during the separation phase (when the separation electrodes 20, 21 are energized). With the wires thus isolated, each assumes the potential of the buffer solution immediately surrounding it, in stepwise increasing manner in accordance with the relative distance of each wire from each of the two separation electrodes.

The upper blotting electrode 42, shown in FIG. 1 as a plate, may assume any of a variety of forms, provided that it meet the criteria of being placed under the liquid level 19 of the buffer solution in the tank during blotting and yet rendered noninterfering with the electrical field created by the separation electrodes 20, 21, as is the lower blotting electrode wire array 41, during the separation phase.

The blotting electrodes 41, 42 will be sized, constructed and arranged to function as plate electrodes approximately equal to or larger than the gel. Gels of various dimensions may be used, limited only by the arrangement of the support brackets 31, 32 and the length and width of the porous support plate 36. To provide for the use of gels of the maximum size, the lower and upper blotting electrodes will either be or simulate plates at least coextensive laterally and longitudinally with the porous support plate 36.

As indicated above, however, there must be a potential difference sustained between the two ends of the gel during the separation phase, and consequently, blotting electrodes which are actual solid plate electrodes in contact with the buffer solution during separation would nullify the field around the gel. The wire array 41 of the present invention serving as the lower blotting electrode avoids this problem. As for the upper blotting electrode, an actual plate may be used, provided that it is one supplied with the capability of being placed alternately in contact and out of contact with the buffer solution. This can be accomplished in any of a variety of ways readily apparent to those skilled in the art. As one example, the plate electrode may be manually raised above or lowered below the liquid level in the tank. As another example, electromechanical means may be provided for raising and lowering the plate electrode. This is readily susceptible to automation. As a third alternative, the height of the electrode plate may be fixed and the liquid level raised and lowered as necessary to establish or break contact. Further possibilities will be readily apparent to those skilled in the art.

An alternative to a plate as the upper blotting electrode is a parallel wire array, similar to that forming the lower blotting electrode. An example of an upper parallel wire array 43 is shown in FIGS. 3 and 4. In accordance with this embodiment, the individual wires in the upper wire array 43 are arranged and connected in such a way that they can be electrically isolated from each other during the separation phase, in a manner identical to the lower wire array 41. Accordingly, the spacing between the wires in the upper array 43 must be sufficiently small that they simulate a plate electrode in terms of the electric field created in the region of the gel 34. This will also be influenced by the distance between the upper and lower wire arrays, and the vertical spacing of the gel 34 from each. As the spacing between adjacent wires in each array narrows, the more closely the array simulates a plate electrode. Other factors to be considered include the fact that the loss in voltage as a function of the distance from the plane of each array lessens as the wires in each array are more closely placed, as well as the fact that the required voltage density within a given array to achieve a given electric field lessens as the wires in that array are placed closer together.

With these considerations in mind, the various physical and electrical parameters of the two wire arrays can be varied considerably. In most cases, best results are obtained with an electric field of from about 1 to about 10 volts per centimeter of distance between the two arrays. Other parameters for best results are wires of a gauge of from about 0.001 inch to about 0.050 inch, wire spacings in any single array of from about 0.5 cm to about 2.5 cm, preferably from about 1.0 cm to about 1.5 cm, and the vertical spacing between the two arrays is from about 2 cm to about 10 cm, preferably from about 3 cm to about 6 cm. It is further preferred that the wires be equally spaced in each array, and that the two arrays be staggered with respect to each other.

As will be readily apparent to those skilled in the art, the choice as to which one among the lower blotting electrode array and the upper blotting electrode in any of its various forms will serve as the anode and which one will serve as the cathode will determine the direction of migration of the solute zones out of the gel, and hence the placement of the blotting membrane 35 either above or below the gel. The preferred arrangement of the gel stack is the one shown in these figures, in which the blotting membrane 35 is positioned below the gel 34. The lower blotting electrode array 41 will accordingly be the anode, causing the blotting migration to occur in the downward direction.

The upper blotting electrode, whether it be a plate or a wire array, will be suspended by conventional means at the appropriate height above the lower wire array. They may be suspended in a movable or removable fashion, or in a fixed fashion, and may be secured to and suspending from the underside of the lid 13 as shown in FIGS. 1. 3 and 4, or the tank side walls. Other possibilities will be readily apparent to those skilled in the art.

The porous support plate 36 serves to support the gel and membrane as flat as possible, and yet to provide as much buffer contact with the gel, and pass as much current through the gel through the buffer solution as possible. With these considerations in mind, the dimensions and pore structure of the plate may vary widely. The pores of course are open pores, providing full fluid communication from one side of the plate to the other. In most cases, pores ranging from about 30 microns to about 300 microns in diameter, preferably from about 50 microns to about 150 microns in diameter, will provide the best results. Likewise, a plate having a thickness of from about 0.1 cm to about 1.0 cm is preferred. Preferred materials for the plate are electrically insulating, hydrophilic materials, such as glass or any of various polymeric materials well known among those skilled in the art.

Similar considerations apply to the upper plate 37. The porosity must be sufficient to provide adequate accessibility of the buffer solution above the gel stack to the upper surface of the gel. The primary function of the upper plate is to flatten the gel against the underlying blotting membrane 35 so that full and uniform contact between the two is maintained, for purposes of ensuring efficient transfer during the blotting phase. This may be accomplished by virtue of the weight of the upper plate. Alternatively, the upper plate may be clamped over the gel, leaving a controlled and uniform height above the lower plate 36, filled with the gel in a manner which avoids excessive pressure on the gel which might distort or close the internal passageways in the gel.

In the arrangement shown in FIG. 3, the heights of both the lower and upper plate are set by the support brackets 31, 32. The lower plate 36 rests on a ledge 44, and the upper plate 37 rests on a shoulder 45, the vertical spacing between the two setting the vertical gap occupied by the gel 34 and membrane 35. This gap may vary depending on the thickness of the gel. In most cases, however, the gap will range from about 0.1 cm to about 2.0 cm. Full contact between the gel and membrane without distortion of the internal gel passageways may be achieved by proper control of the gel thickness.

When the separation electrodes 20, 21 are wire electrodes, as shown in the various figures, the height of these wires will be arranged at mid-height with respect to the gap. With the dimensions indicated in the last paragraph, the wire electrodes will thus be about 0.05 cm to about 1.0 cm above the upper surface of the lower plate 36.

When the cell is operating in the blotting mode, care must be taken to prevent gas bubbles formed at the wires in the lower wire array from resting or accumulating beneath the membrane and thus interfering with the electric current along the membrane surface. The hydrophilic nature of the lower porous plate 36 assists in this regard, by promoting the passage of air bubbles through it, thus facilitating the initial charging of the cell with buffer solution in a manner free of air bubbles. As for the gas bubbles generated by hydrolysis at the lower electrode wires 41, various possibilities exist for preventing them from entering the porous plate and coming into contact with the membrane. One such possibility is shown in FIG. 1, in which a circulation pump 50 is aimed at the gap between the wire array 41 and the ledge 44 defining the location of the bottom surface of the support plate 36. Any bubbles thus rising from the wires are continually swept away.

Another possibility is the placement of a porous barrier between the wires 41 and the ledge 44. The barrier 51 is shown in FIGS. 3 and 4. In this embodiment, the barrier is secured to the support brackets 31, 32 and spans the entire width of the cell, underlying completely the gel stack 33. The barrier sheet contains pores of sufficient size to permit full passage of the buffer solution and all ions contained in it, and yet small enough to prevent passage of gas bubbles. In most applications, the pores ranging from about 0.5 micron to about 20 microns, preferably from about 1 micron to about 5 microns, in diameter will provide the best results. A wide variety of materials, hydrophilic and electrically insulating, may be used; cellophane is one example. A vertical gap is shown between the barrier sheet 51 and the lower surface of the support plate 36, providing sufficient clearance to assure that full circulation of the buffer solution and migration of buffer ions is permitted. For best results, this gap will be at least about 0.2 cm, preferably from about 0.5 cm to about 1.0 cm.

An example of an electrical circuit which will serve the purposes of the present invention is depicted in FIGS. 5 and 6, representing the separatory and blotting modes of operation, respectively.

The upper portions of these figures, designated FIGS. 5a and 6a, represent the separation electrode portion of the circuit. The cell is represented by the outer dashed line rectangle 55, and the gel is represented by the inner dashed line rectangle 56. The separation electrodes 20, 21 are depicted from views taken along their axes. The line 57 joining the separation electrodes 20, 21 represents the path of the current passing through the buffer and gel (showing as well the resistance which the current encounters) while the separation electrodes are energized. A set of parallel switches 58, 59 joins these electrodes to a voltage source 60 which supplies a $V_1$ across the electrodes in the separatory mode, resulting in a current as indicated by the arrow 61.

The blotting electrode portion of the circuit is shown in the lower halves of the figures. FIGS. 5b and 6b. Here the blotting electrodes are shown, including four upper blotting electrodes 62 and four lower blotting electrodes 63, again shown from views taken along their axes. As in the case of the separation electrodes, lines 64 are shown joining the upper and lower blotting electrodes, these lines not representing actual wiring but rather the path of the blotting current through the buffer and gel including the resistance raised by both.

A set of upper diodes 65 and lower diodes 66 serve the function of electrically insulating the blotting electrodes from each other during the separatory mode (FIG. 5b), by preventing current flowing from one to the next. A set of parallel switches 67, 68 on this blotting portion of the circuit is open during the separatory mode and closed during the blotting mode (FIG. 6b), at which time it joins the blotting electrodes to a voltage source 69 which supplies a voltage $V_2$, divided by four in this case, across each opposing set of blotting wires.

The foregoing is offered primarily for purposes of illustration. It will be readily apparent to those skilled in the art that numerous variations, substitutions, and other types of modifications in the structural and electrical components and operational procedures described herein may be made without departing from the spirit and scope of the invention.

What is claimed is:

1. Apparatus for both electrophoretic separation and blotting, comprising:
    a liquid receptacle defined by a floor and raised sides;
    first and second electrode wires defined as separation electrodes, affixed to the interior of said liquid receptacle along opposing raised sides thereof, at a preselected height above said floor;
    a first parallel array of electrode wires defined as lower blotting electrodes, affixed to the interior of said liquid receptacle along said floor;
    a second parallel array of electrode wires defined as upper blotting electrodes, and means for suspending said upper blotting electrodes inside said liquid receptacle above said lower blotting electrodes;
    switching means for switching between (a) electrical isolation of said lower blotting electrodes from one another and said upper blotting electrodes from one another and (b) maintenance of said lower blotting electrodes at equal potentials with each other and said upper blotting electrodes at equal potentials with each other;
    a flat porous plate of electrically insulating hydrophilic material sized to fit inside said liquid receptacle, and means for supporting said flat porous plate in said liquid receptacle above said lower blotting electrodes such that the upper surface of said flat porous plate is about 0.05 cm to about 1.0 cm below said preselected height while forming no barrier to electric current flow between said first parallel array of electrode wires and said first and second separation electrodes.

2. Apparatus in accordance with claim 1 in which said flat porous plate has pores of from about 30 microns to about 30 microns in diameter.

3. Apparatus in accordance with claim 1 in which said flat porous plate has pores of from about 50 microns to about 150 microns in diameter.

4. Apparatus in accordance with claim 1 further comprising means for preventing gas bubbles generated during the passage of an electric current through said lower blotting electrodes from accumulating underneath said flat porous plate.

5. Apparatus in accordance with claim 4 in which said gas bubble preventing means is comprised of a barrier between said lower blotting electrodes and said flat porous plate when so supported, said barrier being permeable to liquid and impermeable to bubbles.

6. Apparatus in accordance with claim 4 in which said gas bubble preventing means is a porous membrane having pores of from about 0.5 micron to about 20 microns in diameter.

7. Apparatus in accordance with claim 4 in which said gas bubble preventing means is a porous membrane having pores of from about 1 micron to about 5 microns in diameter.

8. Apparatus in accordance with claim 4 in which said gas bubble preventing means is a porous membrane positioned at least about 0.2 cm below the lower surface of said flat porous plate when said flat porous plate is so supported.

9. Apparatus in accordance with claim 4 in which said gas bubble preventing means is a porous membrane positioned about 0.5 cm to about 1.0 cm below the lower surface of said flat porous plate when said flat porous plate is so supported.

10. Apparatus in accordance with claim 4 in which said gas bubble preventing means is a cellophane sheet suspended above said lower blotting electrodes and about 0.5 cm to about 1.0 cm below the lower surface of said flat porous plate when said flat porous plate is so supported.

11. Apparatus in accordance with claim 1 in which flat porous plate has pores of from about 30 microns to about 300 microns in diameter said apparatus further comprising a porous membrane having pores of from about 0.5 micron to about 20 microns in diameter, positioned at least about 0.2 cm below the lower surface of said flat porous plate when said flat porous plate is so supported.

12. Apparatus in accordance with claim 1 in which said flat porous plate has pores of from about 50 microns to about 150 microns in diameter, said apparatus further comprising a porous membrane having pores of from about 1 micron to about 5 microns in diameter, positioned 0.5 to about 1.0 cm below the lower surface of said flat porous plate when said flat porous plate is so supported.

13. Apparatus in accordance with claim 4 in which said gas bubble preventing means is comprised of means for continuously circulating buffer solution between said lower blotting electrodes and said flat porous plate when so supported.

14. Apparatus in accordance with claim 1 in which said flat porous plate has a thickness of from about 0.1 cm to about 1.0 cm.

15. Apparatus in accordance with claim 1 in which said flat porous plate is defined as a first flat porous plate, and said apparatus further comprises a second flat porous plate of electrically insulating hydrophilic material sized to fit inside said liquid receptacle.

16. Apparatus in accordance with claim 15 in which said first and second flat porous plates are both substantially rectangular and are substantially identical to each other in length and width.

17. Apparatus in accordance with claim 15 in which said flat porous plate is defined as a first flat porous plate, and said apparatus further comprises a second flat porous plate of electrically insulating material sized to fit inside said liquid receptacle and means for supporting said second flat porous plate above and parallel to said first flat porous plate to define a gap therebetween of from about 0.1 cm to about 2.0 cm.

18. Apparatus in accordance with claim 17 in which said means for supporting said first and second porous plates are arranged such that said first and second porous plates when so supported are at equal distances below and above said first and second electrode wires, respectively.

19. Apparatus for both electrophoretic separating and blotting, comprising:
a liquid receptacle defined by a floor and raised sides;
a parallel array of electrode wires defined as lower blotting electrodes, affixed to the interior of said liquid receptacle along said floor;
a flat porous plate of electrically insulating material sized to fit inside said liquid receptacle, said flat porous plate having an upper surface suitable for supporting a slab gel, and means for supporting said flat porous plate in said liquid receptacle above said lower blotting electrodes at a preselected height above said floor;
an upper blotting electrode, and means for suspending said upper blotting electrode inside said liquid receptacle above said lower blotting electrodes;
first and second separation electrodes, affixed to the interior of said liquid receptacle along opposing raised sides thereof, and arranged and constructed to form a uniform electric field in a plane at a preselected distance above said preselected height;
switching means for switching between (a) electrical isolation of said lower blotting electrodes from one another and (b) maintenance of said lower blotting electrodes at equal potentials with each other; and
means for continuously circulating buffer solution between said lower blotting electrodes and said flat porous plate when so supported, thereby preventing gas bubbles generated during the passage of an electric current through said lower blotting electrodes from accumulating underneath said flat porous plate.

* * * * *